US009828599B2

(12) United States Patent
Nagraj et al.

(10) Patent No.: US 9,828,599 B2
(45) Date of Patent: Nov. 28, 2017

(54) METHODS OF SELECTING BINDING-ELEMENTS AND USES THEREOF

(71) Applicant: General Electric Company, Schenectady, NY (US)

(72) Inventors: Nandini Nagraj, Clifton Park, NY (US); Radislav Alexandrovich Potyrailo, Niskayuna, NY (US); Andrew David Pris, Altamont, NY (US); John Richard Nelson, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 926 days.

(21) Appl. No.: 14/030,386

(22) Filed: Sep. 18, 2013

(65) Prior Publication Data

US 2015/0080226 A1 Mar. 19, 2015

(51) Int. Cl.
*C40B 30/04* (2006.01)
*C12N 15/10* (2006.01)
(Continued)

(52) U.S. Cl.
CPC ..... *C12N 15/1034* (2013.01); *C12N 15/1048* (2013.01); *C12Q 1/6811* (2013.01); *G01N 33/53* (2013.01); *G01N 33/5308* (2013.01); *H04N 1/3232* (2013.01); *H04N 1/32309* (2013.01); *H04N 1/32352* (2013.01); *H04N 1/40* (2013.01); *H04N 1/60* (2013.01); *C40B 30/04* (2013.01); *H04N 2201/0094* (2013.01); *H04N 2201/327* (2013.01);
(Continued)

(58) Field of Classification Search
None
See application file for complete search history.

(56) References Cited

U.S. PATENT DOCUMENTS 5,683,916 A 11/1997 Goffe et al.
5,714,320 A 2/1998 Kool
(Continued)

FOREIGN PATENT DOCUMENTS

EP 2589657 A1 5/2013
WO 2007117444 A2 10/2007
WO 2011060557 A1 5/2011

OTHER PUBLICATIONS

Wang et al., "Ultrasensitive Detection of Protein Using an Aptamer-Based Exonuclease Protection Assay", Analytical CHemistry, vol. No. 76, Issue No. 19, pp. 5605-5610, Oct. 1, 2004.
(Continued)

*Primary Examiner* — Christian Boesen
(74) *Attorney, Agent, or Firm* — Pabitra K. Chakrabarti

(57) ABSTRACT

Methods for selecting a binding-element are provided. The method comprised of different steps. A first mixture is formed using at least one target molecule and a plurality of oligomers, followed by incubating the first mixture to form a second mixture comprising at least one target-bound oligomer and at least one target-unbound oligomer. Then a first accelerator is added to cleave the target-unbound oligomer and the target-bound oligomer is separated from the target molecule. This is followed by addition of a second accelerator for ligation, and a third accelerator for amplification followed by sequencing and post sequence analysis to select the binding-element.

21 Claims, 7 Drawing Sheets

(51) Int. Cl.
 G01N 33/53 (2006.01)
 H04N 1/32 (2006.01)
 H04N 1/40 (2006.01)
 H04N 1/60 (2006.01)
 C12Q 1/68 (2006.01)
(52) U.S. Cl.
 CPC .......... H04N 2201/3233 (2013.01); H04N 2201/3271 (2013.01); H04N 2209/00 (2013.01)

(56) References Cited

U.S. PATENT DOCUMENTS

| | | |
|---|---|---|
| 6,258,275 B1 | 7/2001 | Freitag et al. |
| 6,287,772 B1 | 9/2001 | Stefano et al. |
| 6,426,086 B1 | 7/2002 | Papahadjopoulos et al. |
| 6,867,268 B2 | 3/2005 | Vaidya et al. |
| 7,157,603 B2 | 1/2007 | Hilbrig |
| 7,371,852 B2 | 5/2008 | Hardeman et al. |
| 2002/0076704 A1 | 6/2002 | Weissman et al. |
| 2002/0155478 A1 | 10/2002 | Nelson et al. |
| 2003/0044794 A1 | 3/2003 | Bandaru et al. |
| 2005/0176940 A1 | 8/2005 | King |
| 2008/0182759 A1 | 7/2008 | West et al. |
| 2008/0293926 A1 | 11/2008 | Hallgren et al. |
| 2009/0075834 A1 | 3/2009 | Doyle et al. |
| 2010/0018876 A1 | 1/2010 | Crothers et al. |
| 2010/0028953 A1 | 2/2010 | Koch et al. |
| 2010/0055068 A1 | 3/2010 | Santerre et al. |
| 2010/0151465 A1 | 6/2010 | Ju et al. |
| 2010/0152056 A1 | 6/2010 | Lopreato |
| 2011/0190483 A1 | 8/2011 | Jayawickramarajah |
| 2011/0251088 A1 | 10/2011 | Lopreato |
| 2012/0010390 A1 | 1/2012 | Van Alstine et al. |
| 2012/0115752 A1 | 5/2012 | Zichi et al. |
| 2012/0322681 A1 | 12/2012 | Kung et al. |

OTHER PUBLICATIONS

Mairal et al., "Aptamers: Molecular Tools for Analytical Applications", Analytical and Bioanalytical Chemistry, vol. No. 390, Issue No. 4, pp. 989-1007, Jun. 21, 2007.
PCT Search Report and Written Opinion issued in connection with corresponding PCT Application No. PCT/US2014/055055 dated Dec. 10, 2014.
Majd et al., "The Affinity Precipitation for the Isolation of Biomolecules", Thesis, Ecole Polytechnique Federale de Lausanne, 2007, pp. 1-146.
Kumar et al. "Smart Polymers: Physical Forms and Bioengineering Applications", Available online at www.sciencedirect.com, Received Feb. 22, 2007, received in revised form May 22, 2007, accepted May 22, 2007, Prog. Polym. Sci. vol. 32, 2007, pp. 1205-1237.
Famulok et al., "Aptamer modules as sensors and detectors", Accounts of Chemical Research, 2011, vol. 44, No. 12, pp. 1349-1358.
Potyrailo et al., "Polymeric Sensor Materials: Toward an Alliance of Combinatorial and Rational Design Tools?", Angew. Chem. Int. Ed. 2006, vol. 45, pp. 702-723.
Kimoto et al., "Generation of high-affinity DNA aptamers using an expanded genetic alphabet", Nature Biotechnology 2013, vol. 31, No. 5, pp. 453-457.
Švitel et al., "Surface plasmon resonance based pesticide assay on a renewable biosensing surface using the reversible concanavalin A monosaccharide interaction", Biosensors Bioelectronics, 2000, vol. 15, pp. 411-415.
Choi et al., "Reusable biosensors via in situ electrochemical surface regeneration in microfluidic applications", Biosensors Bioelectronics, 2009, vol. 25, pp. 527-531.
Xu et al., "Label-free impedimetric thrombin sensor based on poly(pyrrole-nitrilotriacetic acid)-aptamer film", Biosensors Bioelectronics, 2013, vol. 41, pp. 90-95.
Radi et al., "Reagentless, Reusable, Ultrasensitive Electrochemical Molecular Beacon Aptasensor", J. Am. Chem. Soc. 2006, vol. 128, pp. 117-124.
Potyrailo, R. A. et al., "Adapting selected nucleic acid ligands (aptamers) to biosensors", Analytical Chemistry, 1998, vol. 70, No, 16, pp. 3419-3425.
Yao, C. et al., "Aptamer-based piezoelectric quartz crystalmicrobalance biosensor array for the quantification of IgE", Biosensors and Bioelectronics 2009, vol. 24, pp. 2499-2503.
Guo, L. et al., "Reusable plasmonic aptasensors:Using a single nanoparticle to establish a calibration curve and to detect analytes", ChemComm 2011, vol. 47, pp. 7125-7127.
Wijesuriya, D. et al., "Regeneration of immobilized antibodies on fiber optic probes", Biosensors & Bioelectronics 1994, vol. 9, pp. 585-592.
Andersson, K. et al., "Identification and optimization of regeneration conditions for affinity-based biosensor assay. A multivariate cocktail approach", Analytical Chemistry, 1999, vol. 71, No. 13, pp. 2475-2481.
Kandimalla, V. B. et al. "Regeneration of ethyl parathion antibodies for repeated use in immunosensor: a study on dissociation of antigens from antibodies", Biosensors and Bioelectronics 2004, vol. 20, pp. 903-906.
Drake, A. W. et al., "A strategic and systematic approach for the determination of biosensor regeneration conditions", Journal of Immunological Methods 2011, vol. 371, pp. 165-169.
Liss, M. et al., "An aptamer-based quartz crystal protein biosensor", Analytical Chemistry, 2002, vol. 74, No. 17, pp. 4488-4495.
Yao, C. et al., "Development of a Quartz Crystal Microbalance Biosensor with Aptamers as Bio-recognition Element", Sensors 2010, vol. 10, pp. 5859-5871.
Bock, L. C. et al., "Selection of single-stranded DNA molecules that bind and inhibit human thrombin", Nature 1992, vol. 355, pp. 564-566.
Chilkoti, A. et al., "Molecular Origins of the Slow Streptavidin-Biotin Dissociation Kinetics", J. American Chemical Society 1995, vol. 117, pp. 10622-10628.
Piran, U. et al., "Dissociation rate constant of the biotin-streptavidin complex", Journal of Immunological Methods 1990, vol. 133, pp. 141-143.
Lin, S. et al, "Characterization of the 'helix clamp' motif of HIV-1 reverse transcriptase using MALDI-TOf MS and surface plasmon resonance", AAnalytical Chemistry, 2000, vol. 72, pp. 2635-2640.
Freitag, R. et al., "Affinity precipitation an option for early capture in bioprocessing." Biotechnology Journal 2007, vol. 2, No. 6, pp. 685-690.
Galaev, I. Y. et al., "Affinity thermoprecipitation: Contribution of the efficiency of ligand-protein interaction and access of the ligand." Biotechnology and Bioengineering 1993, vol. 41, No. 11, pp. 1101-1106.
Miyakawa, S. et al., "Structural and molecular basis for hyperspecificity of RNA aptamer to human immunoglobulin G", 2008 RNA, vol. 14, No. 6, pp. 1154-1163.
Soh, N. et al., "Affinity Precipitation Separation of DNA Binding Protein Using Block Conjugate Composed of Poly (N-isopropylacrylamide) Grafted Double-Stranded DNA and Double-Stranded DNA Containing a Target Sequence". Analytical Sciences 2002, vol. 18, No. 12, pp. 1295-1299.
Walter, J.-G. et al., "Aptamers as affinity ligands for downstream processing", Engineering in Life Sciences 2012, vol. 12, No. 5, pp. 1-11.
Arnold et al., "Novel thermo-responsive fucose binding ligands for glycoprotein purification by affinity precipitation", Received Jun. 25, 2013, 19 pages.
Tuerk et al., "Systematic Evolution of Ligands by Exponential Enrichment: RNA Ligands to Bacteriophage T4 DNA Polymerase", Science, pp. 505-510, vol. 249, 1990.
Thomas Hermann et al., "Adaptive Recognition by Nucleic Acid Aptamers", Feb. 4, 2000; 6 pages.

(56) References Cited

OTHER PUBLICATIONS

Stacey L. Clark et al., "Aptamers as analytical reagents", Electrophoresis 2002, 23, 1335-1340.
Dua et al., "Patents on SELEX and Therapeutic Aptamers", Recent Patents on DNA & Gene Sequences, pp. 172-186, vol. 2, Issue 3, 2008.
Manjula Rajendran et al., "Selecting Nucleic Acids for Biosensor Applications", Combinatorial Chemistry & High Throughput Screening, 2002, 5, 263-270.
Sefah et al., "Development of DNA Aptamers Using Cell-SELEX", Nature Protocols, pp. 1169-1185, vol. 5, Jun. 1, 2010.
Cheng et al., "In vivo SELEX for Identification of Brain-penetrating Aptamers", Molecular Therapy Nucleic Acids, vol. 2, 2013.
Scott E Osborne et al., "Aptamers as therapeutic and diagnostic reagents: problems and prospects", Current Opinion in Chemical Biology 1, 1997, pp. 5-9.
Sulay Jhaveri et al., "In vitro selection of signaling aptamers", Nature Biotechnology, vol. 18, Dec. 2000, pp. 1293-1297.
Tim Sampson ; "Protecting intellectual property rights in SELEX and aptamers"; World Patent Information, 2003, 7 Pages.
Subash Chandra Bose Gopinath, "Methods developed for SELEX" , Anal Bioanal Chem, 2007, pp. 171-182.
U.S. Appl. No. 14/043,895, filed Oct. 2, 2013, Radislav Alexandrovich Potyrailo et al.
U.S. Appl. No. 14/043,887, filed Oct. 2, 2013, Anthony John Murray et al.

METHODS OF SELECTING BINDING-ELEMENTS AND USES THEREOF

STATEMENT REGARDING FEDERALLY SPONSORED RESEARCH & DEVELOPMENT

This invention was made with Government support under contract number HSHQDC-10-C-00206 awarded by the Department of Homeland Security. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 5, 2013, is named 268087-1_SL.txt and is 2,508 bytes in size.

FIELD OF INVENTION

The invention generally relates to methods for selecting binding-elements. The methods specifically relate to methods for selecting nucleic acid binding-elements to provide specific target binding.

BACKGROUND

Selection of binding elements, such as antibodies, nucleic acid aptamers or peptide aptamers, in relatively short spans of time remains a key challenge, particularly with regard to fine tuning the selectivity, sensitivity and specificity for a desired target. Antibodies are valued for their high selectivity and affinity, however, they are also susceptible to degradation, aggregation, modification or denaturation. In addition, antibodies for therapeutic applications require production in mammalian cell lines; which is an expensive and complex process, having a probability of variation from batch to batch.

Engineered protein binders based on stable protein scaffolds have proved to be a successful strategy for production of affinity ligands since these ligands are smaller than antibodies, and are relatively stable and can be synthesized in microbial production systems. While many of these binders might be unsuitable for therapeutic applications because of their potential immunogenicity, they have found application as binders in analytical, diagnostics and chromatographic applications.

Binding-elements, such as aptamers are oligonucleotide affinity ligands that are selected for their high affinity binding to molecular targets. A variety of binding-elements have been developed based on nucleic acids, such as deoxyribonucleic acids (DNA), ribonucleic acids (RNA) or peptide nucleic acids (PNA). Discovery of oligonucleotide binders involves selection processes from a library of DNA, RNA or modified nucleic acid oligomers involving multiple cycles. An example of oligonucleotide binder selection is SELEX (systematic evolution of ligands by exponential enrichment), wherein multiple rounds of selection and amplification are carried out to develop binding-elements with the desired affinity and selectivity. Additionally, non-SELEX methods have also been developed for aptamer discovery, such as the NECEEM (non-equilibrium capillary electrophoresis of equilibrium mixtures) based method that relies on non-equilibrium capillary electrophoresis of equilibrium mixtures. While the SELEX approach is the most reliable and extensively used method for discovery of aptamers to date, SELEX method is labor-intensive, time-consuming and expensive. The NECEEM based method is less time consuming, however, the method is completely dependent on the use of a capillary electrophoresis instrument, sensitivity of the detector, size and charge of the target molecule.

Therefore, there is a need to develop an alternative approach for discovery of binding-elements having high affinity towards a variety of targets for a desired application in a short span of time.

BRIEF DESCRIPTION

An embodiment of a method of selecting a binding-element is provided, wherein the method comprises providing a first mixture comprising at least one target molecule and a plurality of oligomers comprising non-complementary end sequences; incubating the first mixture to form a second mixture comprising at least one target-bound oligomer and at least one target-unbound oligomer; adding an accelerator to cleave the target-unbound oligomer; and separating the target-bound oligomer from the target molecule to down select the binding-element.

An embodiment of a method of selecting a binding-element comprises providing a first mixture comprising at least one target molecule and a plurality of oligonucleotides; incubating the first mixture to form a second mixture comprising at least one target-bound oligonucleotide and at least one target-unbound oligonucleotide; adding a first accelerator to cleave the target-unbound oligonucleotides; separating the target-bound oligonucleotides from the target molecule forming target specific oligonucleotides; adding a second accelerator to ligate the target-specific oligonucleotides; and adding a third accelerator for amplifying the target-specific oligonucleotides to form a binding-element.

Another embodiment of a method of selecting a binding-element, comprises providing a first mixture comprising at least one target molecule, and a plurality of oligopeptides; incubating the first mixture to form a second mixture comprising at least one target-bound oligopeptide and at least one target-unbound oligopeptide; adding an accelerator to cleave the target-unbound oligopeptide; and separating the target-bound oligopeptide from the target molecule to down select the binding-element.

In some embodiments, a method of selecting a binding-element comprises providing a first mixture comprising at least one target molecule, and a plurality of peptide nucleic acids; incubating the first mixture to form a second mixture comprising at least one target-bound peptide nucleic acid and at least one target-unbound peptide nucleic acid; adding accelerator to cleave the target-unbound peptide nucleic acid; and separating the target-bound peptide nucleic acid from the target molecule to down select the binding-element.

An embodiment of a kit for selecting a binding-element is provided, wherein the kit for selecting a binding-element specific for a target, comprises a plurality of nucleic acid oligomers; and a first accelerator comprising an enzyme selected from an exo-nuclease, an endo nuclease, a ligase, a polymerase or a combination thereof, wherein the target comprises a protein, a peptide, a carbohydrate, a small molecule, a large molecule, a drug, an epitope or combinations thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
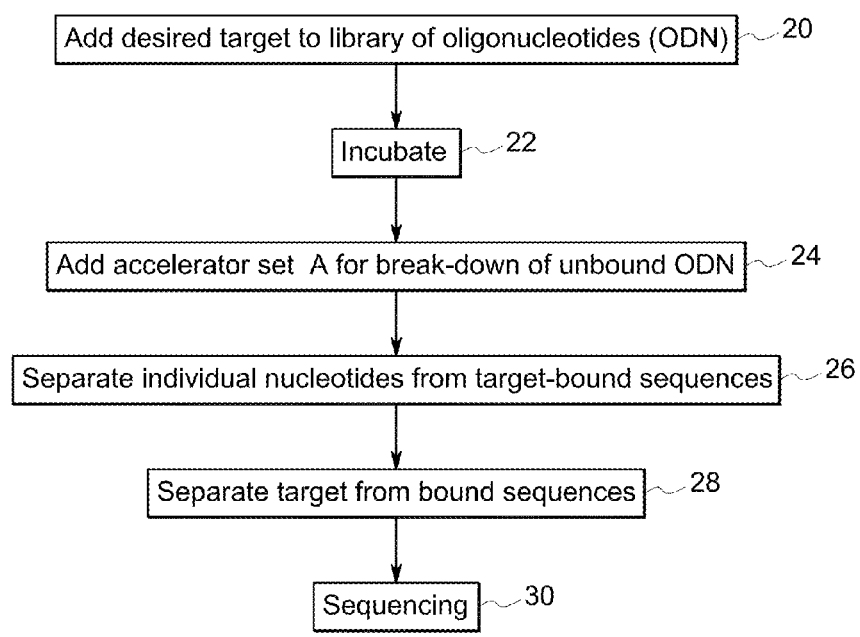
FIG. 1 is a flow chart showing method of selecting a binding-element for specific target molecules in accordance with one embodiment of the invention.

The methods and kits for selecting oligomer-based binding-elements using the target molecule are provided. The selected binding-elements have high specificity for the target molecule. When used the term "high specificity", refers to the binding-elements that have specificity for the target molecule that is >90% compared to when there is no specificity for the target. The selection methods are reliable and suitable for applications such as affinity purification of the target molecules from a population of molecules having structure similar to the target.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein the term "nucleotide" or "nucleotide base" refers to a nucleoside phosphate. The term includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleotide triphosphate (dNTP) or a ribonucleotide triphosphate (NTP). The nucleotides may be represented using alphabetical letters, for example, A denotes adenosine (e.g., a nucleotide containing the nucleobase, adenine), C denotes cytosine, G denotes guanosine, and T denotes thymidine.

As used herein, the term "oligonucleotide" refers to oligomers of nucleotides or derivatives thereof. The term "nucleic acid" as used herein refers to polymers of nucleotides or derivatives thereof. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right. The oligonucleotides/nucleic acids may be a DNA, RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof. The oligonucleotide refers to a short linear oligonucleotide that may include 5 to 30 nucleotides. The oligonucleotides may also interchangeably used herein as "oligomers" or "short oligomers". The oligonucleotide may be an RNA sequence, a DNA sequence, or a chimeric sequence. The oligonucleotide may contain natural, synthetic, or modified nucleotides. Both the upper and lower limits of the length of the oligonucleotide are empirically determined. The lower limit on oligonucleotide length is the minimum length that is required to form a transient complex upon binding with the target molecule under desired reaction conditions. Very short oligonucleotides (usually less than 3-4 nucleotides long) do not form thermodynamically stable complex with target molecule under such conditions. Generally, suitable oligonucleotide lengths are in the range of about 4 to about 30 nucleotides long.

As used herein, the terms "amplification", "nucleic acid amplification", or "amplifying" refer to the production of multiple copies of a nucleic acid template, or the production of multiple nucleic acid sequence copies that are complementary to the nucleic acid template, for example, a ligated oligonucleotide.

As used herein, the term "target molecule" refers to a molecule that is desired to be bound to one or more short oligomers present in the reaction mixture. For example, the target molecule may comprise a protein, a post-translationally modified protein, a peptide, a carbohydrate or a synthetic peptide. The target molecule is the molecule of interest, which either needs to be separated and purified out from a mixture of molecules or needs to be quantified or characterized. In one or more embodiments, the target molecules are also represented as templates.

As used herein the term "reaction mixture" or "mixture" refers to the combination of reagents or reagent solutions, which are used to carry out a chemical analysis or a biological assay. The reaction mixture or mixture may include oligomers, target molecules, ligase, buffer reagents, chelating agents or water.

As used herein the term "accelerator" refers to enzymes that are either synthesized chemically, or derived from a biological origin that catalyze chemical and/or biochemical reactions. In some embodiments, the accelerator includes one or more physical causes that activates the reaction, either chemical or biochemical. The accelerators may include organometallic complexes, metal salts, other chemical reagents. The accelerators may include biological enzymes comprising nucleases, kinases, ligases, polymerases. In some embodiments, the accelerators may include environmental conditions comprising heat, light, temperature or combinations thereof. In embodiments of the method comprises multiple accelerators, such as a first accelerator, a second accelerator or a third accelerator. The first accelerator may be a nuclease, protease, or peptidase. The second accelerator may be a ligase. The third accelerator may be a polymerase.

One or more embodiments of the invention are directed to methods for selection of oligomer based binding-elements for affinity binding assays. The term "binding element" refers to herein as an oligomer-based component that efficiently binds to a target molecule through one or more binding sites. The binding element may include an aptamer. In one or more embodiments, the binding element is nucleic acid aptamer, such as DNA aptamer or RNA aptamer; peptide-aptamer or peptide nucleic acid aptamer.

In some embodiments, the methods for selecting a binding-element comprise providing a first mixture comprising at least one target molecule and a plurality of oligomers comprising non-complementary end sequences; incubating the first mixture to form a second mixture comprising at least one target-bound oligomer and at least one target-unbound oligomer. Then an accelerator is added to the second mixture to cleave the target-unbound oligomer(s) wherein the accelerator refers herein as a first accelerator. Followed by cleaving of the target-unbound oligomers, the target-bound oligomer(s) from the target molecule are separated followed by sequencing and post sequence analysis to down select the binding-element.

As noted, the first mixture comprises at least one target molecule, wherein the target molecule may be an organic molecule, an inorganic molecule, a synthetic molecule or combinations thereof. In one or more embodiments, the target molecule may be a protein, a post-translationally modified protein, a peptide, a carbohydrate, a drug, a carrier, a small molecule, an adapter, an epitope or combinations thereof. The target molecule may comprise a single entity or a multiple entity. In one example, a cell-surface protein is a single entity, which has only one binding motif and that can be a single entity target.

As noted, the target molecule may comprise a multiple entity, such as, one or more cell-surface proteins have epitopes that are associated with multiple single entities. For example, the target may be a specific combination of epitopes, such as, a multi-subunit protein complex or a section of a cell surface comprising the multi-subunit protein. In another example, when the target molecule comprises a multiple entity, the non-limiting examples of a multiple entity include surface of a cell, surface of a virus, surface of a tissue, at least two outer regions of a folded polymer molecule, at least two outer regions of a folded biopolymer molecule, a surface of an inorganic amorphous material, and a surface of an inorganic crystalline material.

In these examples the binding-element for such a target has a single binding motif or more than one binding motif.

The term "carrier" refers to a compound that may attach to one or more drug, protein, peptide, carbohydrate, lipid, genetic material or small molecule for targeted delivery and controlled release. The carrier may include a synthetic compound or a natural compound isolated from different sources. The carrier may be a nanoparticle. In one embodiment, the target molecule is a protein or peptide, such as thrombin. In some embodiments, the target molecule may include carbohydrate, for example anthrose, lactose or fructose. The target molecules may be present in a solution, an extract or a formulation, which may be added to the oligomers at a concentration, ranged between 1 pM and 1 mM. In some embodiments, the target molecule may be present on a surface of a large molecular assembly. In some other embodiments, the target molecule may be present inside a large molecular assembly.

As noted, the first mixture comprises a plurality of oligomers comprising non-complementary end sequences, wherein the oligomers comprise oligonucleotides, peptides, chemical oligomers or combinations thereof. In some embodiments, the oligomers comprise oligonucleotides, wherein the oligonucleotides comprise deoxyribonucleic acids (DNA), ribonucleic acids (RNA), peptide nucleic acids (PNA) or their analogues (e.g., phosphorothioate analogue) or combinations thereof. The oligonucleotides or nucleic acids may also include modified bases, and/or backbones (e.g., modified phosphate linkage or modified sugar moiety). Non-limiting examples of synthetic backbones that confer stability and/or other advantages to the nucleic acids may include peptide nucleic acid or analogues thereof.

As noted, the oligomers comprise non-complementary end sequences; the term "non-complementary" refers to the sequences which are not complementary or not substantially complementary to each other. For example, the oligonucleotide sequence comprises a sequence represented by a letter sequence (W)x(N)y(S)z, wherein x=2, y=3 and z=1, represents an oligonucleotide sequence WWNNNS, wherein W is the 5' terminal nucleotide and S is the 3' terminal nucleotide. As the end sequences, such as (W)x and (S)z are non-complementary sequences, the structure exclude the probability of forming a secondary structure of the binding element.

In some embodiments, the (W)x, (N)y, and (S)z are completely random sequences. As noted, the oligonucleotide sequence may comprise "random sequence" or a "complete random sequence" or a "chimeric random sequence". Thus the random sequence is a random mixture of oligonucleotide sequences, consisting of every possible combination of nucleotides within the sequence. For example, a hexamer random sequence may be represented by a sequence or (N)6. A hexamer random DNA sequence consists of every possible hexamer combinations of 4 DNA nucleotides, A, T, G and C, resulting in a random mixture comprising $4^6$ (4,096) unique hexamer DNA oligonucleotide sequences. Random binding-element sequence may be effectively used to bind a target when the target molecule is unknown. The binding element sequence does not require any additional specific nucleotide repeats or sequences unlike the sequences used for various currently used aptamers to generate specific conformation for binding target or for identification.

In some embodiments, the sequence (W)x(N)y(S)z comprises a specific sequence to only one end, either at the 5' end or at the 3' end. The binding element with random sequence with a short specific marker sequence at the one end helps sequence selection during analysis and that ensures increasing diversity of the binding elements. For example, (W)x is a short stretch of specific sequence that helps in selection during sequence analysis of multiple sequences. The sequences of 70 mer and 90 mer with a specific 5' marker sequence is used for Examples 1, 2 and 3 of the specification. The specific sequence at only one end helps in easy selection during sequence analysis of the binding element unlike the design of known aptamers with specific sequences which required for amplification, identification or secondary structure formation.

In one or more embodiments, the oligomers refer to smaller fragments of oligonucleotides and may comprise 4 nucleotides to 60 nucleotides. In some embodiments, the oligonucleotides comprise 4 to 1000 nucleotides. A set of short oligonucleotides are desirable for the present method. Suitable lengths of the oligomers may be in the range of 4 nucleotides to 60 nucleotides, 4 nucleotides to 30 nucleotides, or 4 nucleotides to 10 nucleotides. In some embodiments, the length of the oligomers is 4 to 7 nucleotides. The oligonucleotides may include but are not limited to, 10 to 20 nucleotides, 15 to 30 nucleotides, 10 to 30 nucleotides, 10 to 25 nucleotides or combinations thereof. In one embodiment, the oligomers containing 6 to 8 nucleotides with randomized sequence are used.

As noted, the methods comprise providing a first mixture comprising at least one target molecule and at least one oligomer, wherein the target molecule and the oligomer are added sequentially or simultaneously to form the first mixture. In some embodiments, a plurality of oligomers is added to one target molecule to form a oligomer-target molecule complex. In some other embodiments, a plurality of oligomers is added to a plurality of target molecules to form a plurality of oligomer-target molecule complexes.

On incubation, the first mixture is converted to a second mixture, wherein the second mixture comprises at least one target-bound oligomer and at least one target-unbound oligomer. In one or more embodiments, the methods further comprise forming an oligomer-target molecule complex, wherein at least one oligomer is bound to the target molecule to form an oligomer-target molecule complex. In some embodiments, a plurality of the oligomers is bound to each of the target molecules to form a complex of oligomers-target molecule. The term "oligomer(s)-target molecule complex" or "oligomer(s)-target complex" is used interchangeably, hereinafter.

In one or more embodiments, the oligomers have affinity for the target molecules. As used herein, the term "affinity" refers to a force of attraction between two or more molecules that helps to keep the molecules in combination. For example, the affinity between enzymes and substrate molecules results in enzyme-substrate complex. The plurality of oligomers may have an attraction for the target molecules, which helps forming the oligomer-target complex. The affinity of the oligomers for the target molecules may enhance the binding efficiency for the target molecules.

As noted, the method comprises forming an oligonucleotides-target molecule complex, the term "oligomers-target complex" refers to a complex wherein a plurality of oligomers are bound to a target molecule. The oligomers may be bound to the target molecules by a variety of interactions including, but not limited to, covalent interaction, ionic interaction, hydrogen bonding, Vander Waal's forces, multivalent binding, cooperative binding, charge-charge interactions, or combinations thereof. In some embodiments, the oligomer-target complex is stabilized by adding a reaction buffer to the mixture. The oligomers may also be modified to provide increased hydrophobicity.

In one or more embodiments, the oligomers bind to a target transiently. The transient binding offers protection of the bound oligomers during digestion of the target-unbound oligomers, and the bound oligomers may dissociate from the target molecule during or after the digestion step. The term "transient interaction" refers to interaction or binding of plurality of oligomers to the target molecule for a short time to form the oligomers-target complex.

In one or more embodiments, the first mixture is incubated at an ambient temperature. In some embodiments, the incubation temperature is in a range from about 20° C. to about 37° C. In one embodiment, the incubation temperature is room temperature of 21° C. The first mixture may be incubated at ambient temperature for about 5 minutes to about 60 minutes. In one embodiment, the first mixture is incubated at ambient temperature for about 30 minutes to form the second mixture.

As noted, the second mixture comprises at least one target-bound oligomer and at least one target-unbound oligomer. The oligomers which are not bound to the target molecules may be referred to as "target-unbound" or "free" oligomers. The target molecule may have one or more sites for which the oligomers have binding affinity. In these examples, plurality of oligomers bound to one target molecule. In some embodiments, all the binding sites of the target molecule are occupied by the oligomers, and the excess oligomers are present in the second mixture as target-unbound oligomers. To down select a binding element, the target-unbound oligomers are cleaved in smaller pieces and removed from the mixture.

The target-unbound oligomer(s) are cleaved by adding a first accelerator to the second mixture. In some embodiments, the accelerator is added separately to the second mixture after forming the oligomer-target complex. In one or more embodiments, the oligomers-target complex, target-unbound oligomers and the first accelerator are mixed using different mixing techniques, such as by pipetting up and down, vortexing, mild shaking, waving or stirring. In some embodiments, the accelerator comprises an enzyme.

As noted, the first accelerator comprises an enzyme, wherein the enzyme induces the cleaving of the target-unbound oligomers. As used herein, the term "cleave" refers to digestion, slicing or cutting the oligomers into smaller pieces. In one or more embodiments, the first accelerator comprises an enzyme, wherein the enzyme comprises nucleases, proteases, peptidases or combinations thereof. In the embodiments, wherein the oligomers are oligonucleotides, the selection of enzymes is based on oligonucleotide digesting enzymes, such as nucleases. In some embodiments, the nuclease includes but is not limited to, endo-nuclease and exo-nuclease. The nucleases are capable of cleaving the oligonucleotides which are not bound to the target. The nucleases are capable of cleaving the oligonucleotides at either 3' end, at 5' end or at internal locations. In some embodiments, wherein the oligomers are proteins or peptides, the selection of enzyme is based on proteins or peptides digesting enzyme, such as protease or peptidase. The peptidase may include pepsin, trypsin, chymotrypsin or combinations thereof. In one or more examples, commercially available proteases are used, such as Proteinase K, trypsin, thrombin, and elastase.

The enzymatic cleavage of target-unbound oligomers is followed by separating the target-bound oligomer. In embodiments, wherein the oligomers are nucleic acids, the enzymatic digestion results in smaller fragments of nucleotides. In embodiments, wherein the oligomers are protein or peptides, the enzymatic digestion results either in smaller fragments of peptides or in amino acids. In some embodiments, the oligomers are chemical oligomers, such as carbohydrates, polymers or dextran. The enzymatic digestion or cleavage of chemical oligomers results in mono-saccharides or di-saccharides, monomers of any polymeric molecules or small organic molecules.

In one or more embodiments, the cleaved, degraded or digested oligomers are separated from the mixture using either a chromatographic technique or alternate separation techniques. The cleaved or digested oligomers may be separated from the mixture using a spin column, gel filtration column, a mesh, a filter unit or combinations thereof. After removing the cleaved oligomers from the second mixture, the oligomer-target molecule complex remains in the mixture.

The target-bound oligomer(s) are separated from the target molecule to down select the binding-element, wherein the separated target-bound oligomer(s) have target specific sites and hereinafter refers as "target specific oligomers". The target specific oligomers are no longer bound to target after separation and further subjected to amplification or sequencing for down selecting the binding element. The target specific oligomers are oligomers having high affinity for binding the target molecules.

In one or more embodiments, the target specific oligomers are separated from the target molecule, target-unbound oligomers or any other impurities present in the second mixture. In some embodiments, the manipulations that disrupt the interaction between the target specific oligomers and the target, may lead to dissociation of the target molecule from the target specific oligomers, enabling recovery of the target specific oligomers using mild elution conditions. In some embodiments, the manipulations that disrupt the structure of the target specific oligomers release the target molecules. In some examples, a dissociation of the target specific oligomers and the target molecule may be achieved by removal of divalent cations that stabilize the binding-element-target-complex by use of a chelator.

As noted, the target-bound oligomers are separated from the target molecule to down select the binding-element. The term "down select" refers to herein a number of downstream processes for selection of the binding element from the target specific oligomers. After separation from the target, the target specific oligomers are further ligated to circularize, followed by amplification and sequencing. The sequence analysis ensures selection of highly specific and high affinity target specific oligomers, which are called "binding element" for the target.

The selected binding elements are subjected to sequencing followed by sequence analysis. Prior to sequencing of the binding-elements, the purification of the reaction mixture may be necessary. The impurities may comprise excess target molecules, excess un-cleaved oligomers or cleaved oligomers. The selection of highly efficient binding-elements may be based on size of the binding-element, number of binding sites for a target present on the binding element, or binding affinity of the binding-element.

One embodiment of the method is illustrated in FIG. 1. In this embodiment, one or more desired target molecules are added to a library of oligonucleotides 20 to form a first mixture. As used herein the term "library", refers to a selection of multiple species in a single repository. For example, an oligonucleotide library refers to multiple oligonucleotide sequences, such as thousands of oligonucleotide sequences, which are present in a single repository for use in multiplexing reactions. The first mixture is incubated 22 to form a second mixture comprising at least one target-bound oligonucleotide and at least one target-unbound oligonucleotide. Then an accelerator set A is added to the second mixture to cleave the target-unbound oligonucleotide(s) 24. The accelerator A may include an enzyme, such as Exonuclease I. Followed by cleaving the target-unbound oligonucleotides, the cleaved oligonucleotides are separated 26. The target-bound oligonucleotide(s) are separated from the target molecule 28, followed by sequencing and post sequence analysis to down select the binding-element 30.

The binding-element may be separated from the impurities by one or more separation techniques. In some embodiments, the separation may be achieved based on the size or chemical properties of the binding-element, target molecules or oligomer-target molecule complex. In some embodiments, the separation techniques may include chromatographic separation or electrophoretic separation. One or more embodiments of the chromatographic separation techniques may comprise gel-filtration chromatography, ion-exchange chromatography, affinity chromatography or combinations thereof. In one embodiment, the chromatographic separation may include affinity chromatography, which may further refine the binding-elements.

The selected binding-elements may be sequenced using sequencing techniques followed by sequence analysis. The binding-element sequences may be analyzed to determine commonality of motifs in the sequences. For example, the sequences of the binding-elements are compared, wherein the sequences that contain oligonucleotide motifs with prevalence greater than ~1% are selected. In some examples, oligonucleotide sequences that have high motif prevalence are synthesized chemically and designed to have a specific sequence at one end of the oligonucleotide sequence. The specific sequence may be designed to have a biotinylated sequence, wherein each biotinylated oligonucleotide is then attached to a streptavidin chip and tested for affinity against the original target molecule.

The embodiments, wherein the oligomers are oligonucleotides, the method of selecting a binding-element, further comprises adding a second accelerator to ligate the target-specific oligonucleotides; and adding a third accelerator for amplifying the target-specific oligonucleotides to form a binding-element. As noted, in some embodiments, the selected target-specific oligonucleotides are subjected to ligation before sequencing, wherein the oligonucleotides are nucleic acids, such as DNA, RNA or PNA sequences. In these embodiments, the target-specific oligonucleotides are separated from the target molecule and other target-unbound cleaved oligonucleic acids followed by addition of another accelerator, which may comprise an enzyme that phosphorylates 5' end of the nucleic acids. In one or more examples, the enzyme is a kinase. In some embodiments, a T4 polynucleotide kinase is used to phosphorylate the 5' end simultaneously.

The methods further comprise ligating the target-specific oligonucleotides to form a circularized binding-element. In one or more embodiments, the second accelerator is added to the phosphorylated nucleic acids, wherein the second accelerator comprises a ligase. In these embodiments, the ligase is added to the 5'-phosphorylated nucleic acids for nucleic acid ligation. The addition of ligase results in self-ligation of a nucleic acid forming circularized nucleic acid. In one or more embodiments, phosphorylated nucleic acids and ligase are mixed using different mixing techniques, such as by pipetting up and down, vortexing, mild shaking, waving or stirring. In one or more embodiments, the ligase is added to the target-specific oligonucleotides to initiate ligation of the ends to form a circularized nucleic acid or circularized binding element using a suitable ligase, such as CircLigase™.

One or more ligases may be selected to ligate the ends of one or more of the binding-elements, such as a thermostable RNA ligase or T3 RNA ligase. For example, CircLigase™ may be used to ligate single stranded DNA into circles without the need for a template. The probability that the two ends of the binding-elements are ligated is enhanced by the proximity of the two ends. In some embodiments, the ligation reaction is concentration dependent. Linear single stranded DNA of greater than 30 bases is circularized by CircLigase™ enzyme, and the reaction conditions are adjusted such that circular concatemers are produced.

In one or more examples of the methods, CircLigase™, RNA ligase or T3 RNA ligase is added to the binding-elements, along with 1× reaction buffer followed by incubation. To achieve complete ligation in the presence of ligases and the reaction buffer, the optimum temperature may be maintained based on the optimal condition for the ligase used. This can be between 0° C. and 37° C. In one embodiment, the optimum temperature may be maintained at room temperature, in some other embodiments, the optimum temperature may be maintained at 30° C., or in some embodiments, the optimum temperature may be maintained at 20° C. In one embodiment, the mixtures are incubated for 1-5 hours at 20° C. In one embodiment, the ligation is achieved by incubating the mixture at 25° C. for 30 minutes.

In one or more embodiments, the method further comprises addition of a third accelerator to the circularized binding-element to amplify the binding-element sequence. The third accelerator may include a polymerase, such as TempliPhi®. In these embodiments, the method further comprises amplifying the circularized binding-element to form an amplified binding-element sequence. In some embodiments, the amplification comprises a polymerase chain reaction (PCR), an isothermal amplification, a rolling circle amplification (RCA) or a multiple displacement amplification. In one embodiment, the amplification of circularized binding-element may be achieved by RCA amplification. Following RCA amplification, the amplified binding-element is subjected to sequencing on a sequencing instrument. In some embodiments, the amplified binding-element sequence determines the target molecules from a sample comprising the target molecules. In these embodiments, the sample comprises target molecules and one or more molecules having similar structure as the target molecule. The term "similar structure" may refer to the structure of the molecules having one or more structural motifs which are structurally identical or have partial similarity, wherein other motifs or domains of the molecules are different.

Post amplification, the amplified binding-elements may be sequenced using sequencing techniques followed by sequence analysis. The binding-element sequences may be analyzed to determine commonality of motifs in the sequences. The sequences of the binding-elements are compared, wherein the sequences that contain oligonucleotide motifs with prevalence are selected. Each of the oligonucleotides is then tested for affinity against the original target molecule using appropriate binding verification techniques including, but is not limited to, fluorescence and surface plasmon resonance (SPR).

Figure 2:
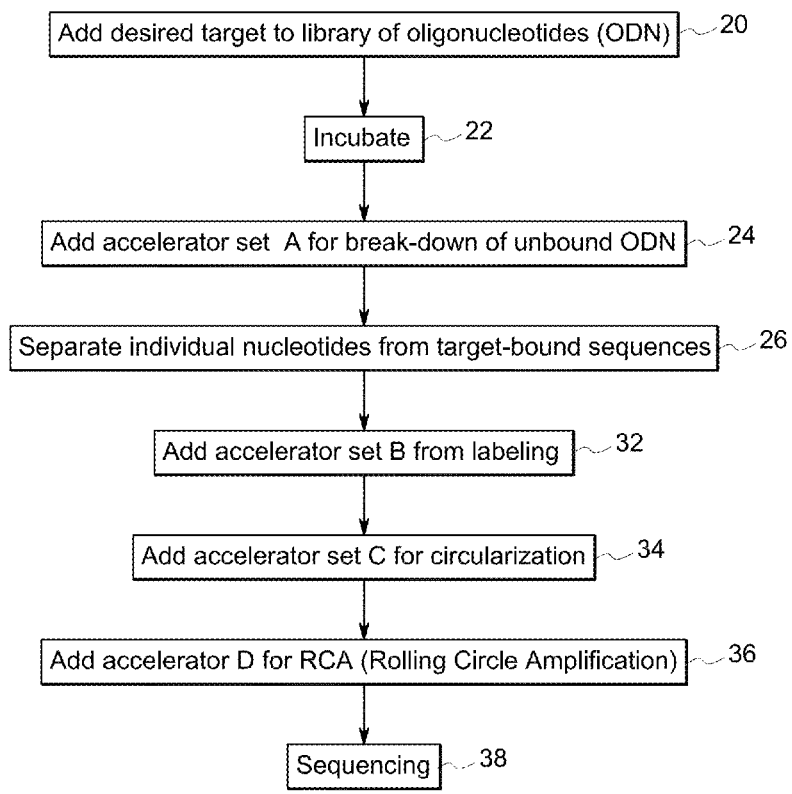
FIG. 2 is a flow chart showing method of selecting a binding-element, ligating, amplifying and sequencing the binding-element in accordance with one embodiment of the invention.

Another exemplary embodiment of the method for selecting binding-element for a specific target, wherein the binding-element is based on nucleic acids. is illustrated in a flow chart of FIG. 2. In an alternative embodiment, some of the steps may be performed simultaneously or in different order.

In some embodiments, one or more steps may be added to the flow chart. In this embodiment, one or more desired target molecules are added to a library of oligonucleotides (such as nucleic acids, e.g. DNA, RNA or PNA) 20 to form a first mixture. The first mixture is incubated 22 to form a second mixture comprising at least one target-bound oligonucleotide and at least one target-unbound oligonucleotide. Then an accelerator set A is added to the second mixture to cleave the target-unbound oligonucleotide(s) 24. As noted, the accelerator A may include an enzyme, such as Exonuclease. Followed by cleaving the target-unbound oligonucleotides, the cleaved oligonucleotides or nucleotides are separated 26. In these embodiments, the binding-elements are separated from the target molecule and other target-unbound cleaved oligonucleotides followed by addition of another accelerator 32, for example, an accelerator B, which may comprise an enzyme that phosphorylates 5' end of the nucleic acids. In one or more examples, the enzyme is a kinase, such as polynucleotide kinase. In one or more embodiments, an accelerator, such as accelerator C is added to the phosphorylated nucleic acids for circularization of the binding-element 34, wherein the accelerator C comprises a ligase. Following circularization, another accelerator may be added, such as accelerator D for amplification of the circularized nucleic acids 36 followed by sequencing of the amplified nucleic acids 38.

The binding-elements are selected, wherein the binding-elements function as affinity ligands and are selected for high affinity binding to molecular targets. The binding-elements may comprise one or more binding moieties for the target molecules. A variety of binding-elements have been developed based on DNA and RNA, wherein the RNA binding-elements tend to be less stable than their DNA counterparts. DNA binding-elements are reliable for their pH and thermal stability, small size (~13 kDa) and potential for high binding capacity and therefore may be used as affinity binders for downstream processing, quantitation and characterization. In some embodiments, the binding-elements are ranging between 15-60 nucleotides in length.

Figure 3:
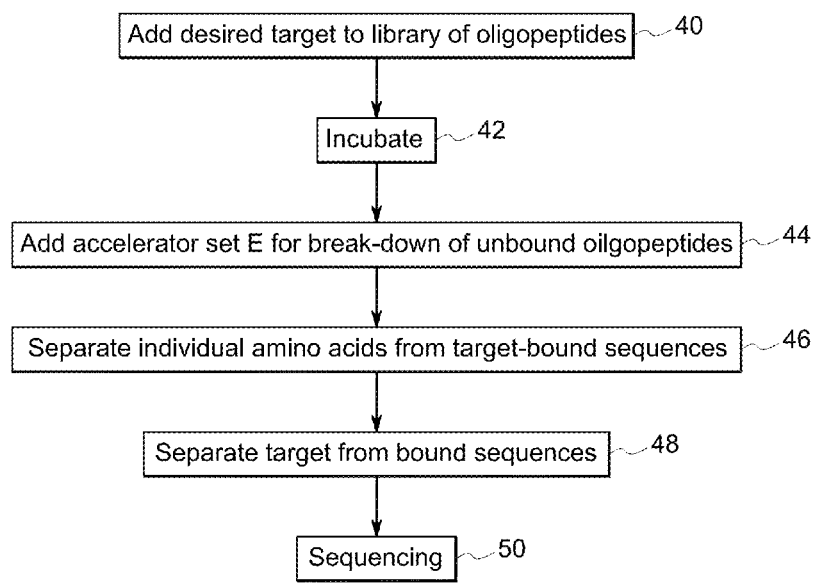
FIG. 3 is a flow chart showing method of selecting a binding-element based on oligopeptides for specific target molecules in accordance with one embodiment of the invention.

FIG. 3 is another flow chart illustrating an exemplary embodiment of a method for selecting a binding element for a specific target, wherein the binding-element is based on proteins or peptides. In an alternative embodiment, some of the steps may be performed simultaneously or in different order. In some embodiments, one or more steps may be added to the flow chart. In this embodiment, one or more desired target molecules are added to a library of oligopeptides 40 to form a first mixture. The first mixture is incubated 42 to form a second mixture comprising at least one target-bound oligopeptide and at least one target-unbound oligopeptide. Then an accelerator set E is added to the second mixture to cleave the target-unbound oligopeptide(s) 44. As noted, the accelerator E may include an enzyme, such as a protease. Followed by cleaving the target-unbound oligopeptide, the cleaved oligopeptide or individual amino acids are separated 46 from target-bound oligopeptides. The target is separated from the target-bound oligopeptide sequence 48 for selecting binding-element, followed by sequencing of the binding-element 50. The selected binding elements are further refined and subjected to sequence analysis. The sequences of the binding-elements are characterized to provide characterized binding-element, which has sufficient affinity for the target molecules.

Figure 4:
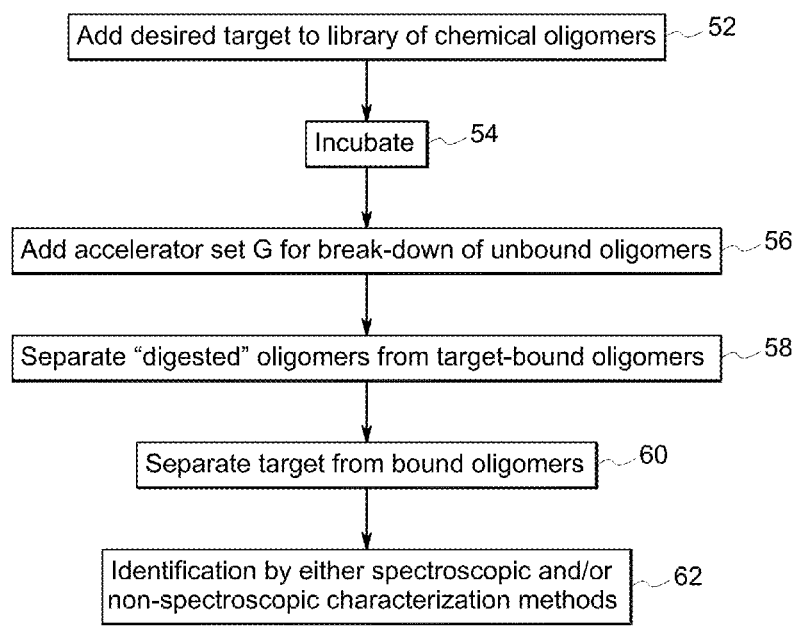
FIG. 4 is a flow chart showing method of selecting a binding-element based on chemical oligomers for specific target molecules in accordance with one embodiment of the invention.

FIG. 4 is another flow chart illustrating an exemplary embodiment of a method for selecting a binding element for a specific target, wherein the binding-element is based on chemical oligomer. In an alternative embodiment, some of the steps may be performed simultaneously or in different order, such as one or more steps may be added to the flow chart. In this embodiment, one or more desired target molecules are added to a library of chemical oligomer 52 to form a first mixture. The first mixture is incubated 54 to form a second mixture comprising at least one target-bound chemical oligomer and at least one target-unbound chemical oligomer. Then an accelerator set G is added to the second mixture to cleave the target-unbound chemical oligomer (s) 56. The accelerator G may include a chemical catalyst, organometallic complex, any other chemical, or controlled environmental conditions that facilitate the digestion or break-down of monomers.

Some nonlimiting examples of controlled chemical conditions that serve as accelerators in this invention include organometallic complexes with metal centers such as Ru, Ir, Ni, Pt, Pd and others. Other nonlimiting examples of controlled chemical conditions that serve as accelerators include ligands such as porphyrins, acetates or EDTA. Other nonlimiting examples of controlled chemical conditions that serve as accelerators in this invention include metal catalysts, including nanoparticles of metals such as Pt, Pd and other transition metals.

Nonlimiting examples of controlled environmental conditions that serve as accelerators include electromagnetic radiation, magnetic field, ionic strength of solution, light, temperature of solution, pH of solution.

Followed by cleaving the target-unbound chemical oligomer, the cleaved chemical oligomer or individual monomers are separated 58 from target-bound chemical oligomer. The target is separated from the target-bound chemical oligomer 60 for selecting binding-element, followed by identification of the binding-element 62 using either spectroscopic or non-spectroscopic characterization methods.

In one embodiment, the starting nucleic acid, peptide or protein 'library' refers to either combinatorial sequence pools or rationally designed sequence pools or completely random nucleic acids or amino acids sequences. In one embodiment the target is incubated with the starting nucleic acid, protein or peptide library and through the use of enzymes that cleave the unbound sequences and or bases, the target-bound sequences are isolated from the rest of the starting nucleic acid, protein or peptide pool. In one embodiment, the target-bound sequences are separated and/or purified from the unbound sequences using gel-based, column-based or precipitation-based methods. For example, the target-bound sequences are purified by anion exchange HPLC.

An embodiment of a kit for selecting a binding-element comprises a first mixture comprising at least one target molecule, and a plurality of oligomers; and at least one accelerator.

In some embodiments of the kit, the target molecule may comprise an organic molecule, an inorganic molecule, a synthetic molecule or combinations thereof. The oligomers comprise oligonucleotides, peptides, chemical oligomers or combinations thereof. The oligonucleotides comprise deoxyribonucleic acids, ribonucleic acids, peptide nucleic acids or combinations thereof. The chemical oligomers may include carbohydrates or polymers.

In some embodiments, the accelerator of the kit comprises an enzyme. The enzyme may comprise a nuclease, a polymerase, a ligase or a combination thereof. Depending on the selection of oligomers, the choice of accelerators may change. For example, when the oligomers comprise nucleic acids, one of the accelerators may comprise of a nuclease.

For another example, when the oligomers comprise peptide or protein, one of the accelerators may comprise of a protease.

Depending on the requirement of product, the accelerator may change. In some embodiments, when the requirement of a product is circularized nucleic acids, then the kit further comprises another accelerator, which includes ligase. The ligase circularizes the product nucleic acid binding-element. In some other embodiments, when the requirement for a product is amplified circularized nucleic acids, then the kit further comprises another accelerator, which includes polymerase. Each and every constituents of the kit may be packaged in one pack or they may be available separately, depending on requirement.

The kit further comprises a matrix to purify the binding element. The kit further comprises one or more buffers for digestion of oligomers, ligation of oligomer, amplification of oligomers or combinations thereof. In some embodiments, a user manual may be supplied with the kit providing direction of use.

EXAMPLES

Materials used: Reagents and buffer: 1× Binding Buffer contained 20 mM Tris, pH 7.4, 100 mM NaCl, 5 mM $MgCl_2$. Stock solution of lactose: 36.95 mM lactose solution was made in 1× binding buffer. The primer-nucleotide solution (primer-nucleotide mix) comprising primer and nucleotides (dNTPs) was used for PCR amplification.

DNA sequences: The following DNA sequences were used (SEQ ID NO: 1) 70 mer sequence: GTA AAA CGA CGG CCA GT $(N)_{53}$, (SEQ ID NO: 2) 90 mer sequence: GTA AAA CGA CGG CCA GT $(N)_{73}$. The PAGE-purified DNA sequences were obtained from Integrated DNA Technologies (IDT), Coralville, Iowa 1 mM stock solutions for each of the sequences were prepared in DI water and stored at −20° C. Aliquots of 10 µM of each individual sequence were prepared in 1× binding buffer and stored at −20° C. These aliquots were used for subsequent experiments.

Enzymes: Exonuclease I (*E. coli*): Obtained from New England Biolabs (M0293L), supplied along with 10× reaction buffer and stored at −20° C. T4 Polynuleotide Kinase (cloned) and 10 mM ATP solution were obtained from Epicentre (Illumina Company) (WI, USA), T4 Polynuleotide Kinase was supplied with 10× reaction buffer and stored at −20° C. CircLigase™ single stranded DNA ligase (ss DNA ligase) was obtained from Epicentre (Illumina Company), supplied with 10× reaction buffer, 2.5 mM ATP and 50 mM $MnCl_2$, and stored at −20° C. Illustra TempliPhi 100 Amplification kit was obtained from GE Healthcare, supplied with a sample buffer, reaction buffer, enzyme mix and positive control DNA, stored at −20° C.

Column: Illustra NAP-5 Columns were obtained from GE Healthcare. Purification, desalting, buffer exchange of oligonucleotides (minimum: 10-mers) using NAP-5 were achieved by gravity flow and the column was stored between 4-30° C.

Example 1. Selection of DNA Based Binding-Elements Using Target Molecules

10 µM DNA was denatured in a boiling water bath for ~3 min and annealed by incubation on ice for ~45 min. Lactose was used as a target molecule. The target and DNA sequences were incubated for the final application of the binders. The following conditions as shown in Table 1, were used for incubation and for isolation of a lactose binder and then incubated at room temperature for 1 hour:

TABLE 1

Protocol for binding reaction

| Constituents | Volume Added | Final Concentration |
|---|---|---|
| 10 µM DNA | 10 µL | 1 µM |
| 36.95 mM Lactose | 2.7 µL | 1 mM |
| 1X binding buffer | 87.3 µL | — |
| Total reaction volume | 100 µL | — |

10.1 µL of 10× Exonuclease I in reaction buffer was added to 100 µL of each of the two solutions, for a final concentration of 1× and the final pH of the resultant solutions were measured to ensure a pH required for Exonuclease I activity. 20 units of Exonuclease I was added to each of the two tubes, followed by heat activation of Exonuclease I by incubating reaction mixture at 37° C. for 30 min. Exonuclease I was deactivated by adding 25 mM EDTA to chelate $Mg^{2+}$, followed by heat inactivation through incubation of the mixture at 80° C. for 30 min.

Figure 5:
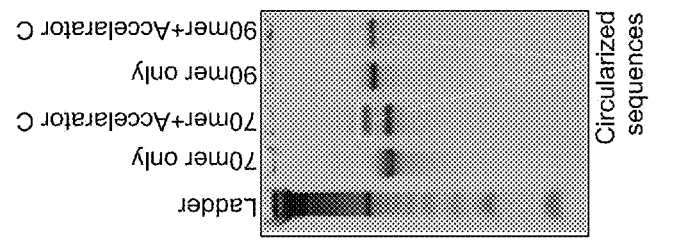
FIG. 5 is a 15% Tris, Boric acid, EDTA (TBE)-Urea denaturing gel showing DNA binding-element.

5 µL aliquot of mixture from previous step was loaded on a 15% TBE-Urea (denaturing) gel and was run for 30 min, followed by staining with SYBR® Gold nucleic acid stain (from Invitrogen). Denaturing PAGE gels post stained with SYBR® Gold nucleic acid stain, imaged on a Typhoon imager for visualization, as shown in FIG. 5. The molecular weight marker (ladder, lane L) and control samples (lanes 1 and 3 for 70 mer and 90 mer respectively) were loaded for comparison. The target-unbound DNA was digested using a nuclease, and the target-bound sequences were separated from the target and loaded on to the gel, as shown the bands in lanes 2 and 4 for 70 mer and 90 mer respectively. The sequences which were bound to the target were not digested by nuclease activity.

Example 2. Phosphorylation of Selected DNA Based Binding-Elements

The same reaction mixture from Example 1 was run through a GE-NAP 5 column to remove digested nucleotides based on size exclusion, according to recommended protocol provided with the column. Appropriate fractions of purified oligonucleotide based binding-elements were collected and subjected to ethanol precipitation. 1/10 volume of 3M sodium acetate, at pH 5.4 was added to the collected fractions. Then 3× volume of 100% ethanol was added and incubated on ice for 20 min, centrifuged at 11,700 rcf at 4° C. for 30 min. The supernatant was removed and subjected to 70% ethanol precipitation followed by incubation on ice for 15 min, and centrifuged. The supernatant was collected and air dried.

The dried binding-element was resuspended in 20 µL of 1× binding buffer followed by phosphorylation of the 5' end using T4 polynucleotide kinase. The following reactants were combined on ice in the order given below in Table 2:

TABLE 2

Protocol for phosphorylation

| Constituents | Volume Added | Final Concentration |
|---|---|---|
| Deionized water | 27 µL | |
| DNA binding-element | 10 µL | |

TABLE 2-continued

Protocol for phosphorylation

| Constituents | Volume Added | Final Concentration |
|---|---|---|
| 10X T4 PNK reaction buffer | 5 µL | 1 X |
| 10 mM ATP solution | 5 µL | 1 mM- |
| T4 Polynucleotide kinase | 3 U | 0.06 U/µL |
| Total reaction volume | 50 µL | — |

Figure 6:
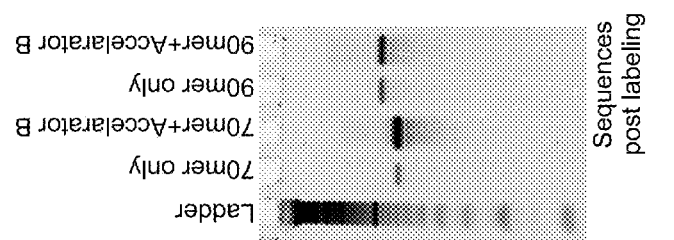
FIG. 6 is a 15% TBE-Urea denaturing gel showing phosphorylated bands for DNA binding-element.

The above reactants were mixed and incubated at 37° C. for 30 minutes followed by heat inactivation of the T4 polynucleotide kinase by incubating at 70° C. for 5 minutes. T4 polynucleotide kinase reaction mixture was loaded and run on a 15% TBE-Urea (denaturing) gel, as shown in FIG. 6. The lane L showed DNA ladder, linear single stranded DNA was loaded to the lanes 1 and 3 for 70 mer and 90 mer respectively and 2 µl of the T4 Polynucleotide Kinase reaction mixtures were on to the lanes 2 and 4 for 70 mer and 90 mer respectively. The gel was run for ~30 min and stained with SYBR® Gold. The phosphorylated DNA binding-element bands are shown in lanes 2 and 4 after treatment with T4 polynucleotide kinase.

Example 3. Ligation of Selected DNA Based Binding-Elements to Form Circularized Binding Element The phosphorylated DNA binding-element obtained from Example 2, was subjected to ligation reaction using CircLigase™ ssDNA ligase using the following protocol in Table 3.

TABLE 3

Protocol for ligation reaction

| Constituents | Volume Added | Final Concentration |
|---|---|---|
| ss DNA binding-element (as template) | 15 µL | |
| 10X CircLigase reaction buffer | 2 µL | 1 X |
| 1 mM ATP solution | 1 µL | 50 µM- |
| 50 mM $MnCl_2$ | 1 µL | 2.5 mM |
| 100 U CircLigase ssDNA Ligase | 1 µL | 5 U/µL |
| Total reaction volume | 20 µL | — |

Figure 7:
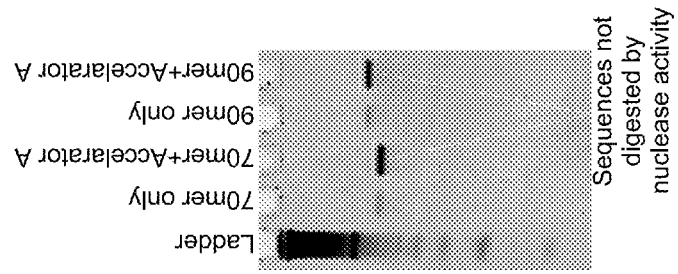
FIG. 7 is a 15% TBE-Urea denaturing gel showing circularized DNA binding-element.

The ligation reaction mixture was incubated at 60° C. for 1 hour followed by heat inactivation of the CircLigase™ single stranded DNA Ligase at 80° C. for 10 minutes. The phosphorylated ssDNA binding-elements for 70 mer and 90 mer were loaded on lanes 1 and 3 respectively of a 15% TBE-Urea (denaturing) gel as control (FIG. 7). 2 µl of the CircLigase™ reaction mixture for 70 mer and 90 mer were loaded on to the lanes 2 and 4 of the gel respectively, followed by running the gel for 30 min. The gel was stained with SYBR® Gold. The circularized ssDNA binding-element product migrates slower the linear single stranded DNA binding-element band, as shown in FIG. 7.

Example 4. Amplification and Sequencing of Circularized DNA Binding-Elements

The remaining linear single-stranded DNA binding-element and linear single-stranded adenylated intermediate from the above ligation mixture were removed by treatment with Exonuclease I. 20 U of Exonuclease I was added, followed by incubation at 37° C. for 30 min.

The sample was ready for Rolling Circle Amplification (RCA). Protocol supplied with the kit was followed to effect RCA amplification. TempliPhi kit components were thawed and placed on ice before starting reaction. 5 μl sample buffer was transferred to the reaction tubes. 1 pg-10 ng of DNA (~0.5 μL) was transferred into the sample buffer, followed by denaturation of the sample by heating at 95° C. for 3 min, followed by cooling to RT for ~30 min. 5 μL of reaction buffer and 0.2 μL of enzyme mix were combined for each TempliPhi reaction, forming TempliPhi premix. 5 μL of the above premix was transferred into annealed DNA. The mixture of premix and annealed DNA was incubated at 30° C. for 18 hrs, followed by heat inactivation of the enzyme by incubating at 65° C. for 10 min and then by cooling to 4° C. The RCA sample was directly then sent to SeqWright for sequencing (SeqWright, part of GE Healthcare).

Structural alignment of 848 sequences obtained for grouping and down selection of potential binders was performed. RNA folding information was used to cluster the 848 sequences and a total of 100 clusters were classified. Folding was carried out using RNA fold, (http://mfold.rna.albany.edu/?q=mfold/RNA-Folding-Form) distance matrix by RNA distance, k-means clustering using k=100 (R packages). Examples of down selected sequences chosen for screening are shown in Table 4.

TABLE 4

Sequences used for various examples

| Binding-element name | SEQ ID NO: | Sequence |
|---|---|---|
| 86_653 | 3 | ACGTATCTTTTCATTGTCCGTGTGGCCCAGTCAAAGGGCTCCATGGGCAGGCT |
| 76_263 | 4 | AGTGAGTAGTTGTCTCGTCAGTTTCTTCGACCGGAGGGGAGCGCGGGGCGGCC |
| 77_549 | 5 | ATCTACGGTTCAGGCCGGGTCGTTCCGGTGCTCGTAATGTACCAGGATGGGCA |
| 96_194 | 6 | TAGCTTCGTCCAAGGTAGGCAATTGCTTCCTTGCCTGGGGTTGCTATGCAACT |
| 26_538 | 7 | TGGGGCCTGAGTAGTGGGTTCTGGTTTTCCATGCCCTTTTTAACCCCTTCTTC |
| 93_574 | 8 | CCTAGTGCATGTGCTTAACTAGATCCGACCGGGCATTGTCAAGAAATGCCGGA |

Figure 8:
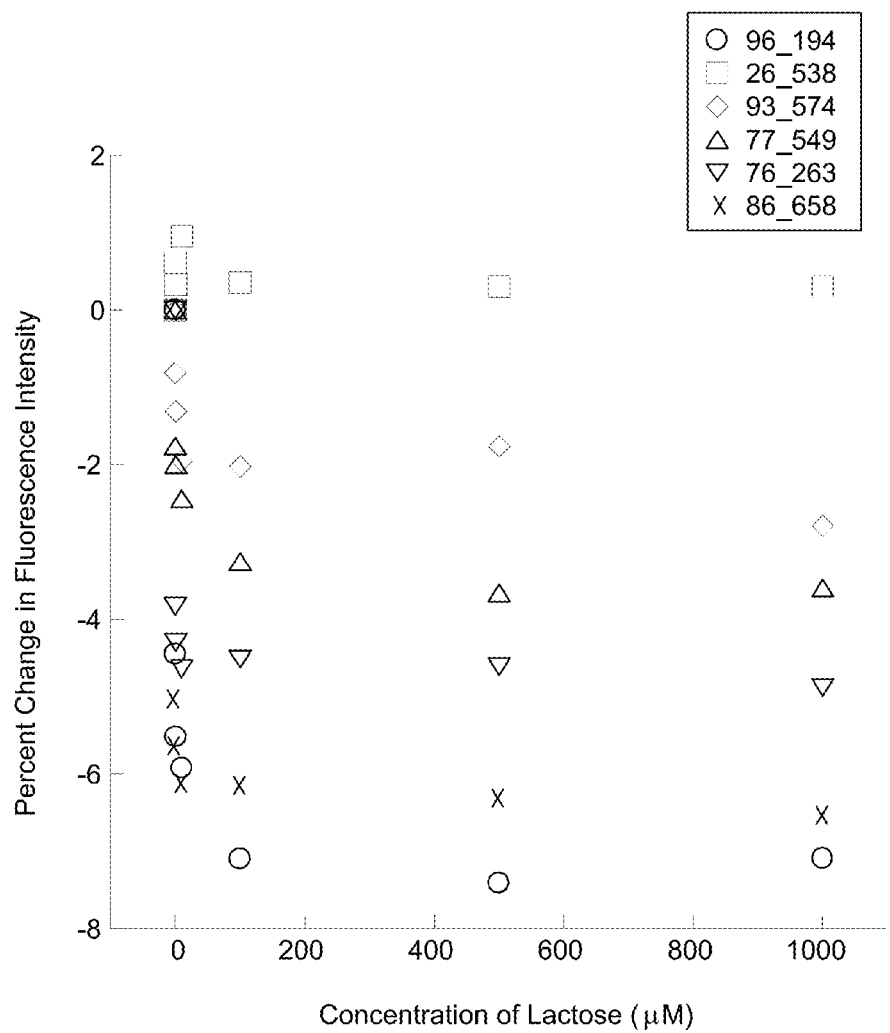
FIG. 8 represents a series of graphs showing binding efficiency of DNA binding-elements with the target molecules.

Example 5. Binding of Target Molecules with the Selected DNA Binding-Elements Oligonucleotide sequences were obtained from Integrated DNA Technologies (Coralville, Iowa). The sequences were 5' labeled with 6-FAM™ (NHS Ester). Lactose was purchased from Carbosynth Limited, United Kingdom. All analyses were performed with a Horiba Jobin Yvon FluoroLog®-3 Spectrofluorometer. Measurements were carried out in binding buffer (20 mM Tris, pH 7.42/100 mM NaCl/5 mM MgCl$_2$). The oligonucleotide sequences were diluted from a 100 μM stock to 25 nM in the binding buffer, denatured in boiling water for 3 minutes and incubated on ice for ~30 minutes. A 200 mM lactose stock solution was prepared by dissolving proper amounts of lactose in the buffer in a 1-mL volume. All solutions with specific concentration were prepared by appropriate dilution from this standard. Concentrations of lactose from 0.5-1000 μM were titrated into the oligonucleotide in buffer. After addition of each solution of different concentration, the reaction mixture was incubated for 3 minutes at room temperature, for binding of lactose with the sequence. A decrease in the fluorescence intensity with increasing concentrations of lactose was observed. The percentage change of the fluorescence intensity from 515-520 nm was determined and plotted against the concentration of lactose as shown in FIG. 8. Different sequences showed varying responses to lactose. The binding element, 96_194 that showed the maximum change in the percent change of fluorescence intensity was used for the specificity studies in the presence of the interferent.

Example 6. Binding of Target Molecule with the Selected DNA Binding-Element in the Presence of the Interferent The binding element, 96_194, was obtained from Integrated DNA Technologies (Coralville, Iowa). The sequence was 5' labeled with 6-FAM™ (NHS Ester). Lactose was purchased from Carbosynth Limited (United Kingdom). All analyses were performed with a Horiba Jobin Yvon FluoroLog®-3 Spectrofluorometer. Measurements were carried out in a binding buffer (20 mM Tris, pH 7.42/100 mM NaCl/5 mM MgCl$_2$). The oligonucleotide sequence was diluted from a 100 μM stock to 25 nM in the binding buffer, denatured in boiling water for 3 minutes and incubated on ice for ~30 minutes. 200 mM stock solutions of lactose and cellobiose were prepared by dissolving proper amounts of lactose and cellobiose in the buffer in a 1-mL volume. All solutions with specific concentration were prepared by appropriate dilution from the stock solution.

Figure 9:
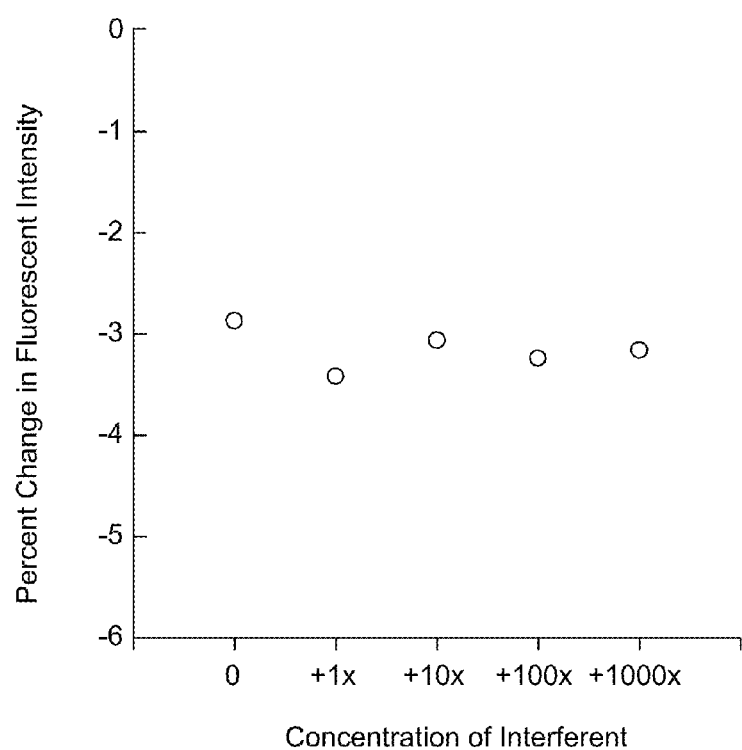
FIG. 9 is a graph showing specific binding efficiency of a binding element with the target molecule in presence of an interferent.

Measurements were performed with a solution containing the oligonucleotide binding element, 96_194, with 1 μM of lactose. The fluorescence signal due to the presence of the 1 μM of lactose and in the absence of interferences is illustrated as the first data point in FIG. 9. The cellobiose was used as an interferent, wherein the cellobiose was titrated at 1× concentration of the target, specifically, 1 μM; 10×, specifically 10 μM; 100×, specifically 100 μM and at 1000×, specifically 1000 μM concentrations. After addition of each solution, the reaction mixture was incubated for 3 minutes at room temperature. A percent decrease of the fluorescence intensity of <1% as compared to the fluorescence signal due to the presence of the 1 μM of lactose upon increasing the concentration of the interferent was observed, which indicates high specificity of the oligonucleotide binder for the target as shown in FIG. 9.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of selecting a binding-element, comprising:
providing a first mixture comprising at least one target molecule and a plurality of oligonucleotides;
incubating the first mixture to form a second mixture comprising at least one target-bound oligonucleotide and at least one target-unbound oligonucleotide;
adding a first accelerator to the second mixture to cleave the target-unbound oligonucleotides;
separating the target-bound oligonucleotides from the target molecule forming target specific oligonucleotides;
adding a second accelerator to the target-specific oligonucleotides to ligate the target-specific oligonucleotides and form a target-specific circularized nucleic acid; and
adding a third accelerator to the target-specific circularized nucleic acid for amplifying the target-specific circularized nucleic acid by isothermal amplification to form a binding-element.

2. The method of claim 1, wherein the first accelerator, the second accelerator, or the third accelerator comprises a biological molecule, a chemical molecule, an environmental condition or combinations thereof.

3. The method of claim 1, wherein the first accelerator comprises an exo-nuclease, an endo-nuclease or a combination thereof.

4. The method of claim 1, wherein the second accelerator comprises a ligase.

5. The method of claim 1, wherein the third accelerator comprises a polymerase.

6. The method of claim 1, wherein the oligonucleotides comprise non-complimentary end sequences.

7. The method of claim 6, wherein the oligonucleotides comprise a random sequence.

8. The method of claim 7, wherein the oligonucleotides further comprise a marker sequence at the one end.

9. The method of claim 1, further comprising phosphorylating a 5' end of the target-specific oligonucleotides before the step of adding the second accelerator.

10. The method of claim 1, wherein the ligation is achieved by incubating the second accelerator and the target specific oligonucleotides between 0 to 37° C.

11. The method of claim 1, wherein the ligation is achieved by incubating the second accelerator and the target specific oligonucleotides at 25° C.

12. The method of claim 1, further comprising sequencing the binding-element to form a binding-element sequence.

13. The method of claim 12, wherein the binding-element sequence comprises a recombination site.

14. The method of claim 12, wherein the binding-element sequence is configured to determine the target molecule from a sample comprising the target molecule by affinity binding.

15. The method of claim 1, wherein the oligonucleotides are modified to provide increased hydrophobicity.

16. The method of claim 1, wherein the separation of the target-bound oligonucleotides is achieved by chemical precipitation comprising acid precipitation, ethanol precipitation, or combinations thereof.

17. The method of claim 1, wherein the separation of the target-bound oligonucleotides is achieved by chromatographic technique, electrophoretic technique or a combination thereof.

18. The method of claim 17, wherein the chromatographic technique comprises gel-filtration chromatography, ion-exchange chromatography, affinity chromatography or combinations thereof.

19. The method of claim 18, wherein the electrophoretic technique comprises gel-electrophoresis.

20. The method of claim 1, wherein the oligonucleotides bind to the target molecule by covalent interaction, ionic interaction, hydrogen bonding, Vander Waal's forces, multivalent binding, cooperative binding, charge-charge interactions, or combinations thereof.

21. The method of claim 1, wherein the oligonucleotides comprise deoxyribonucleic acids, ribonucleic acids, peptide nucleic acids or combinations thereof.

\* \* \* \* \*

SEQUENCE LISTING

<160> NUMBER OF SEQ ID NOS: 8

<210> SEQ ID NO 1
<211> LENGTH: 70
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(70)
<223> OTHER INFORMATION: a, c, t, g, unknown or other

<400> SEQUENCE: 1
gtaaaacgac ggccagtnnn nnnnnnnnnn nnnnnnnnnn nnnnnnnnnn nnnnnnnnnn      60 nnnnnnnnnn                                                              70

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(90)
<223> OTHER INFORMATION: a, c, t, g, unknown or other

<400> SEQUENCE: 2
gtaaaacgac ggccagtnnn nnnnnnnnnn nnnnnnnnnn nnnnnnnnnn nnnnnnnnnn      60
nnnnnnnnnn nnnnnnnnnn nnnnnnnnnn                                       90

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgtatcttt tcattgtccg tgtggcccag tcaaagggct ccatgggcag gct             53

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtgagtagt tgtctcgtca gtttcttcga ccggagggga gcgcggggcg gcc             53

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atctacggtt caggccgggt cgttccggtg ctcgtaatgt accaggatgg gca             53

<210> SEQ ID NO 6
<211> LENGTH: 53
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 6
tagcttcgtc caaggtaggc aattgcttcc ttgcctgggg ttgctatgca act          53

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggggcctga gtagtgggtt ctggttttcc atgccctttt taacccctc ttc           53

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctagtgcat gtgcttaact agatccgacc gggcattgtc aagaaatgcc gga          53
```